United States Patent [19]

Tiffany

[11] Patent Number: 4,872,878
[45] Date of Patent: Oct. 10, 1989

[54] OPTICAL BRIGTHENER IN AN INTRAOCULAR LENS

[75] Inventor: John S. Tiffany, Ventura, Calif.

[73] Assignee: Dennis T. Grendahl, Shorewood, Minn.

[21] Appl. No.: 53,840

[22] Filed: May 26, 1987

Related U.S. Application Data

[63] Continuation-in-part of Ser. No. 26,631, Mar. 17, 1987.

[51] Int. Cl.$^4$ ............................................. A61F 2/16
[52] U.S. Cl. ............................... 623/6; 623/901;
    8/507; 8/638; 351/160 R; 351/160 H
[58] Field of Search ............... 8/467, 507, 648, 638;
    250/519.1; 351/160 R, 160 H, 163, 166;
    523/106, 107; 623/4, 5, 6, 901

[56] References Cited

U.S. PATENT DOCUMENTS

| 4,238,524 | 12/1980 | La Liberte et al. | 8/507 |
| 4,250,315 | 2/1981 | Poncioni | 548/217 |
| 4,257,692 | 3/1981 | Le Naour-Sene | 351/159 |
| 4,402,579 | 9/1983 | Poler | 623/6 |
| 4,636,212 | 1/1987 | Posin et al. | 623/6 |

FOREIGN PATENT DOCUMENTS

| 0136882 | 8/1983 | Japan | 8/507 |

*Primary Examiner*—Richard J. Apley
*Assistant Examiner*—Paul Prebilic
*Attorney, Agent, or Firm*—Hugh D. Jaeger

[57] ABSTRACT

The ultraviolet screening of a silicone rubber intraocular lens can be enhanced by the addition of an optical brightener. The optical brightener also serves to reduce any apparent yellow tint that may occur. The optical brightener is incorporated into the preformed silicone lens by immersing it in a solution containing the optical brightener and an ultraviolet screening agent.

3 Claims, No Drawings

OPTICAL BRIGTHENER IN AN INTRAOCULAR LENS

This application is a continuation-in-part of copending application Ser. No. 026,631, filed Mar. 17, 1987.

BACKGROUND OF THE INVENTION

1. Field of the Invention

This invention relates to the field of foldable or elastometric implantable intraocular lenses composed primarily of silicone rubber and, more particularly, pertains to a method of extending the spectral range through which these lenses block ultraviolet radiation.

2. Description of the Prior Art

Plastic materials have been rendered resistant to passage of ultraviolet radiation by the addition of certain chemical compounds. Typical compounds used to impart ultraviolet screening properties fall primarily into one of two classes, hydroxybenzophenones or hydroxybenzotrizoles. These materials are effective in plastics in blocking transmission of 90% of the ultraviolet radiation below a wavelength of 400 nm when used at concentrations below 1% in a plastic sheet 1 mm thick.

Many of the same ultraviolet screening agents may also be mixed into silicone rubber used to produce foldable intraocular lenses. However, if these agents are mixed into the silicone rubber before it is cured by means of heat and pressure, they may cause undesirably weak and soft lenses. Additionally, when silicone lenses are treated to prevent fogging when immersed in water, some of the screening agents may be lost by leaching from the silicone matrix. Lastly, the commonly used screening agents do not absorb light at 400 nm when used at practical levels in silicone rubber.

The shortcomings of excessive yellowing and reduced ultraviolet absorption at 400 nm are minimized in the lenses of the present invention which are made using diffusion to incorporate into the lens a combination of an ultraviolet screening agent and an optical brightener after it has been shaped and cured.

SUMMARY OF THE INVENTION

The lenses themselves are preformed of any silicone material customarily used in their fabrication.

Illustrative are McGhan NuSIL MED-6210 A/B, Shin-Etsu KE1935 A/B, Petrarch Systems PSW 2398 A/B. These materials are all either resin-reinforced dimethyl siloxanes or resin-reinforced copolymers of dimethyl and diphenyl siloxanes containing 4–12% by weight of diphenyl siloxane.

Preferred for use as McGhan NuSIL MED-6210 A/B or Shin-Etsu KE1935 A/B.

The lenses are made by conventional means, ordinarily molding or casting.

The ultraviolet screening agents can be o-hydroxybenzophenones, o-hydroxybenzotriazoles and substituted phenylformamidines. The screening agents can be used alone or in combination.

The optical brightener which is the subject of this invention is a substituted bisbenzoxazole preferably one such as 2,2'-(2,5-thiophenediyl)bis(5-tertbutylbenzoxazole).

DESCRIPTION OF THE PREFERRED EMBODIMENTS

Lenses are made according to the invention by first preparing a solution of a screening agent and an optical brightener in an organic liquid. Any liquid may be used, provided the liquid will dissolve the required amount of materials, will not significantly degrade the lens material and is physiologically acceptable. Illustrative are lower alcohols such as methanol, ethanol, and isopropanol; lower ketones such as propanone and butanone; ethyl acetate; tetrahydrofuran; and aromatics such as benzene, toluene, and xylene.

Isopropanol is preferred.

The concentration of the screening agent and optical brightener in the liquid is dictated by the nature of the silicone used to fabricate the lens, and must be such that the solution has a higher concentration of absorbers than the lens material. Ordinarily, a concentration of 0.01–0.5% by weight of screening agent and 0.01–0.1% by weight of optical brightener will give a solution having the requisite concentration.

A preformed lens is then immersed in the solution, or otherwise brought into contact with it, and is then held at a temperature of 20°–40° C. until the solution and lens reach osmotic equilibrium, as determined by the ultraviolet absorption at 400 nm reaching a constant value. This ordinarily takes 2–10 days. The lens is then separated from the solution, rinsed and dried to constant weight, and is then ready for use.

EXAMPLE

A solution was prepared by dissolving 0.0136 g of Uvinul D-49 and 0.0027 g of Uvitex OB in 12.77 ml of isopropanol.

A piece of cured silicone rubber 2 mm thick and weighing 1.3 grams was then immersed in the solution for six days at 25° C. It was then removed and dried at 40° C. to constant weight. Its ultraviolet absorbence was found to be one absorbence unit at 398.5 nm. The rubber was colorless and showed no change in hardness. It remained clear when immersed in water or balanced salt solution.

Various modification can be made to the present invention without departing from the apparent scope thereof.

I claim:

1. A method for incorporating an ultraviolet screening agent and an optical brightener into a preformed silicone rubber intraocular lens, the method comprising:
   a. preparing a solution of an ultraviolet screening agent and an optical brightener in an organic liquid, the concentration of each in the solution being such that the solution has a higher osmotic pressure than the lens material;
   b. bringing the lens and the solution into contact with each other until the lens and solution reach osmotic equilibrium;
   c. separating the lens and the solution; and,
   d. drying the lens.

2. The method of claim 1 wherein the optical brightener is a substituted bis benzoxazole.

3. The method of claim 2 wherein the optical brightener is 2,2'-(2,5-thiophenediyl)bis(5-tert.butyl-benzoxazole).